United States Patent [19]
Cremer et al.

[11] Patent Number: 5,998,799
[45] Date of Patent: Dec. 7, 1999

[54] ENVIRONMENTAL CABINET

[75] Inventors: Nigel David Cremer; Anthony Clifford Flory, both of Craven Arms, United Kingdom

[73] Assignee: C & W Specialist Equipment Limited, United Kingdom

[21] Appl. No.: 09/018,290

[22] Filed: Feb. 4, 1998

[30] Foreign Application Priority Data

Feb. 8, 1997 [GB] United Kingdom .................... 9702606

[51] Int. Cl.⁶ .................................................... H01J 37/32
[52] U.S. Cl. .................................. 250/504 R; 250/432 R; 250/493.1; 250/495.1
[58] Field of Search ........................... 250/504 R, 493.1, 250/494.1, 495.1, 492.1, 429, 430, 431, 432 R

[56] References Cited

U.S. PATENT DOCUMENTS 4,698,507  10/1987  Tator et al. ............................. 250/429
4,931,655  6/1990  Yoshida et al. ....................... 250/492.1

*Primary Examiner*—Kiet T. Nguyen
*Attorney, Agent, or Firm*—Ira S. Dorman

[57] ABSTRACT

An environmental cabinet is described for simulating the effects of extended outdoor weathering on a sample material, the outdoor weathering effects including subjecting the sample material to cycles of at least the application of a corrosive solution and exposure to electromagnetic radiation. The cabinet comprises a chamber (11) for containing a sample material to be tested and a source (55) of electromagnetic radiation for subjecting the sample material within the chamber to cycles of radiation. Spray device (19) provides a cyclic spray of a corrosive solution to be deposited on the sample material within the chamber. Control unit subjects the sample material within the chamber to electromagnetic radiation and corrosive solution in a cyclic manner. The source (55) of electromagnetic radiation is disposed within a radiation transparent shield (57) passing through and sealed to the chamber.

30 Claims, 4 Drawing Sheets

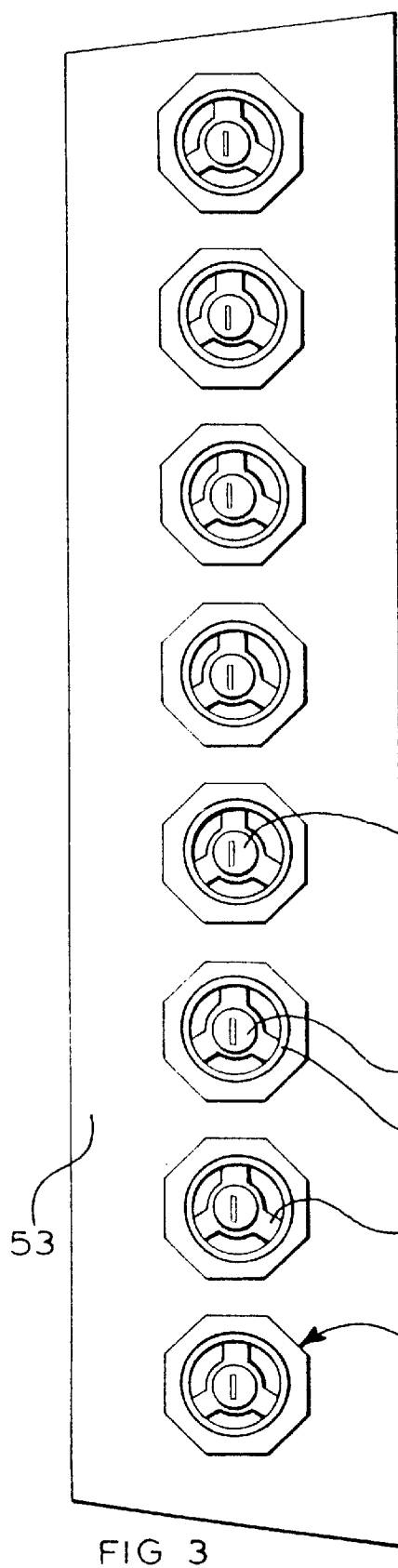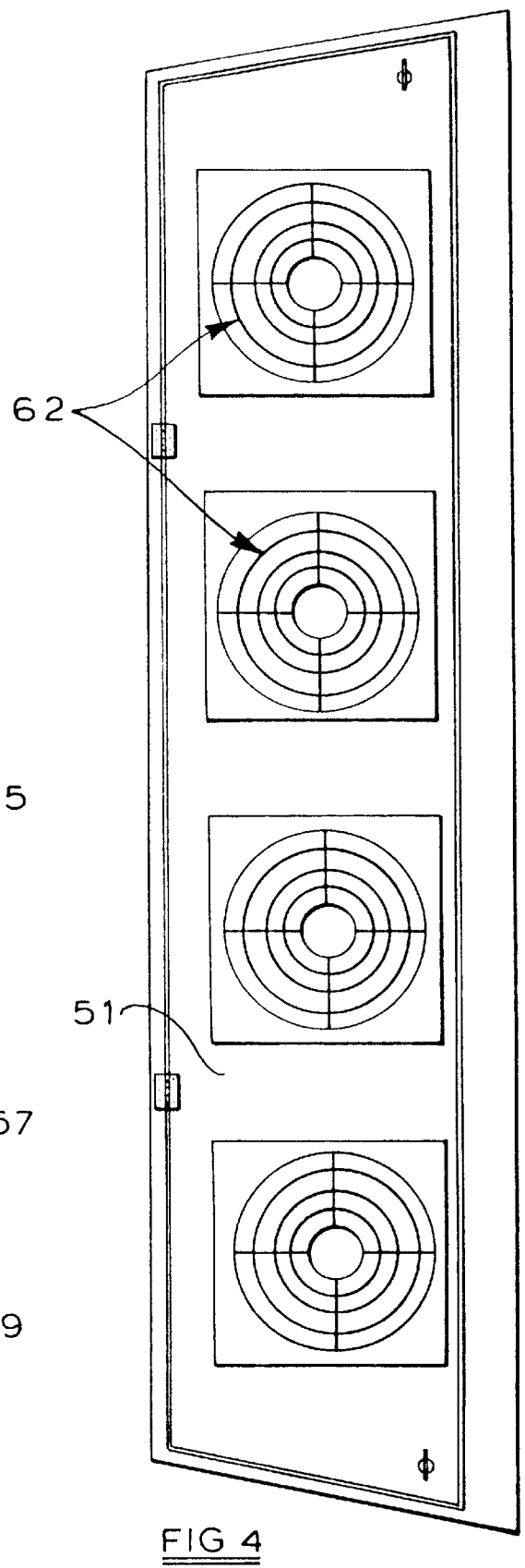

ENVIRONMENTAL CABINET

The present invention is concerned with an environmental cabinet for simulating the effects of extended outdoor weathering on materials such as paint, plastics and textiles.

DESCRIPTION OF PRIOR ART

It is well known to subject materials to cyclic environmental conditions in a testing chamber in order to determine the effect of weathering on the materials. Environmental conditions may include electromagnetic radiation, for example in the form of ultra-violet or infra-red radiation, humidity, heat and corrosive conditions such as those attributable to salt.

However, it is difficult to combine certain environmental conditions in a single cabinet. In particular, it has not until now been practicable to combine electromagnetic (UV or IR) radiation with corrosive (salt) weathering cycles in a single cabinet. The reason for this is that salt solution penetrates the smallest gap in the chamber walls and an electromagnetic radiation cycle requires the provision of an electrical power supply which inevitably becomes corroded by the salt solution and leads to failure of the cabinet. It is difficult to seal the sources of electromagnetic radiation to prevent salt and humidity from attacking the terminations of the radiation source because the service life of these sources is such that they require replacement from time to time. It is also difficult to prevent a build-up of salt crystal deposits on the radiation source, which will have a detrimental effect on the radiation output.

There is therefore a demand for an environmental cabinet which is able to provide weathering cycles that include subjecting a material sample to be tested in a chamber thereof at least to the application of a corrosive solution and exposure to electromagnetic radiation.

OBJECT OF THE INVENTION

It is therefore an object of the present invention to overcome these disadvantages of known environmental cabinets.

SUMMARY OF THE INVENTION

According to the present invention there is provided an environmental cabinet for simulating the effects of extended outdoor weathering on a sample material, the outdoor weathering effects including subjecting the sample material to cycles of at least the application of a corrosive solution and exposure to electromagnetic radiation, which cabinet comprises:

a chamber for containing a sample material to be tested;

a source of electromagnetic radiation for subjecting the sample material within the chamber to cycles of radiation;

spray means for providing a cyclic spray of a corrosive solution to be deposited on the sample material within the chamber; and control means for subjecting the sample material within the chamber to electromagnetic radiation and corrosive solution in a cyclic manner, wherein the source of electromagnetic radiation is disposed within a radiation transparent shield passing through the chamber and sealed thereto.

The source of electromagnetic radiation may be mounted in an openable cover of the chamber.

The source of electromagnetic radiation may be generally cylindrical, for example in the form of a tubular lamp.

The source of electromagnetic radiation may be adapted to emit ultra-violet and/or infra-red radiation. The ultra violet radiation may be in the range from about 280 to about 400 nm, for example in the range from about 280 to about 315 nm and/or in the range from about 315 to 400 nm.

Means may be provided for passing air between the source of electromagnetic radiation and the shield.

The radiation transparent shield may be in the form of a sleeve, such as a tubular sleeve, with the source of electromagnetic radiation extending therethrough. Spacer means may be provided to support the source of electromagnetic radiation in a spaced manner within the sleeve. Means, such as a sprinkler, may be provided for passing a cleaning fluid, such as water, over the outer surface of the radiation transparent shield. Where a plurality of sources of radiation, and therefore a plurality of radiation transparent shields, are provided means may be provided for accumulating the cleaning fluid passing over one radiation transparent shield and for distributing the cleaning fluid over a further radiation shield. Where the radiation shields are arranged generally one above the other, the accumulating and distributing means may comprise an inclined member positioned beneath one radiation transparent shield and adapted to receive cleaning fluid from the one radiation transparent shield, the inclined member being provided with a plurality of apertures for distributing accumulated cleaning fluid over a further radiation transparent shield disposed therebeneath.

For a better understanding of the present invention and to show more clearly how it may be carried into effect reference will now be made, by way of example, to the accompanying drawings in which:

BRIEF DESCRIPTION OF THE DRAWINGS

FIG. 3 is an end elevational view of an inner end plate of the cover of the cabinet;

FIG. 4 is an end elevational view of an outer end plate of the cover of the cabinet.

DESCRIPTION OF PREFERRED EMBODIMENT

Figure 1:
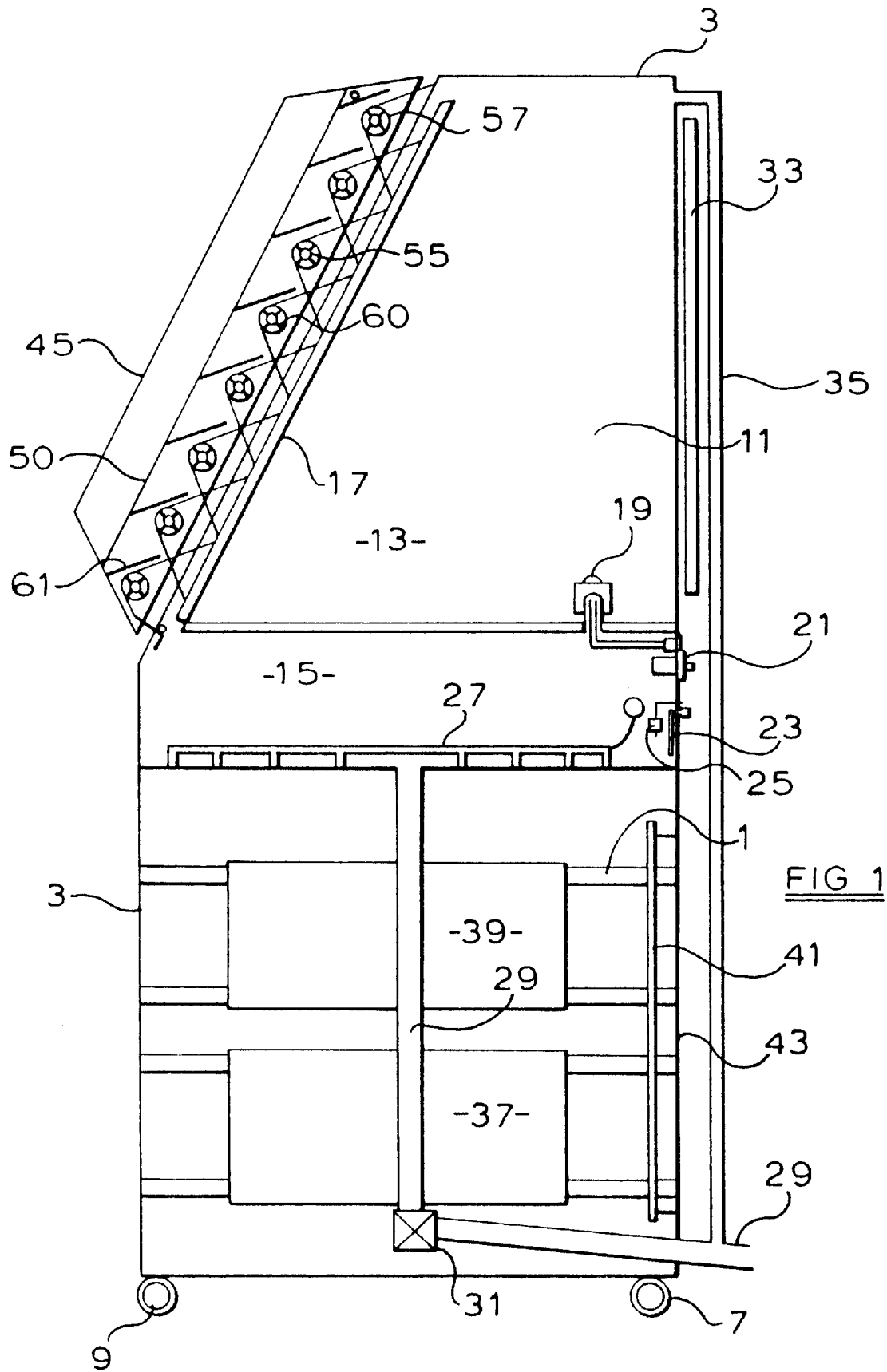
FIG. 1 is a sectional view through one embodiment of an environmental cabinet according to the present invention.

The environmental cabinet shown in FIG. 1 comprises a frame 1, for example of box section mild steel tube, covered with panelling 3, for example of coated mild steel. The cabinet is mounted on four castors 7, 9, two rear castors 7 being unbraked and two front castors being braked so as to enable the cabinet to be moved to a desired location and then locked in position.

Mounted in the upper region of the frame 1 is a chamber 11, for example of glass fibre reinforced plastics material, within which testing of samples takes place. The chamber 11 is open at the front thereof and is divided into an upper portion 13 and a lower portion 15 for producing various test cycles.

A sample support rack 17 is mounted in the upper portion 13 of the chamber for supporting a plurality of test samples (not shown). The test samples may be, for example, metallic or non-metallic and may have an inorganic or an organic coating.

The sample support rack 17 is positioned in the front region of the chamber and is arranged at an angle of about 60 degrees to the horizontal. Also mounted in the upper portion 13 of the chamber, rearwardly of the sample support rack 17, is an atomising nozzle 19 for creating a mist of a corrosive ionised solution within the chamber 11.

Behind the rear wall of the upper portion 13 of the chamber is provided a panel heater 33 for heating the contents of the upper portion. Further panel heaters (not shown) are provided outside the side walls of the upper portion of the chamber. Each panel heater is rated in the range from 400 to 700 Watts, the heating element being protected by and insulated between two electrically insulating boards. Externally of each heater panel is a thermally insulating board to direct heat from the heating element into the upper portion 13 of the chamber 11.

Positioned in the lower portion 15 of the chamber 11 is a series of air purge nozzles 21 for introducing air under pressure in the range from about 0.3 to 1.5 bar into the lower portion of the chamber. Also positioned within the lower portion 15 of the chamber is a water inlet 23 for a humidity bath and a float switch 25 for limiting the level of water in the bath. A heater 27 is mounted on the base of the lower portion 15 of the chamber 11 for heating water forming the humidity bath. The heater 27 is in the form of a 2 kW TEFLON coated immersion element supported above the bottom of the lower portion 15. The TEFLON plastics sheath enables the heater to resist chemical attack. The base of the lower portion 15 of the chamber 11 is provided with a drain 29 of polyvinylchloride material, the drain incorporating a drain valve 31 to regulate the flow of liquid out of the lower portion of the chamber.

An upper drain 35 extends from the upper region of the upper portion 13 of the chamber 11 to the downstream side of the drain 29.

Mounted in the lower region of the frame 1 are a power chassis 37, a control chassis 39, an air and water chassis (not shown) and starter circuitry 41 for a source of electromagnetic radiation as will be described in more detail hereinafter, the starter circuitry 41 being mounted on the inside of a lower rear inspection/access panel 43.

The power chassis 37 receives and distributes a single phase electrical power supply, for example rated at 13 amps. The air and water chassis receives and distributes a supply of water regulated to a pressure of substantially 2 bar and a supply of clean, dry compressed air regulated to a pressure of substantially 4 bar. The air and water chassis also includes an air pressure regulator and pressure gauge for controlling and indicating the pressure of air supplied to the atomising nozzle 19. There is also a 24 volt DC variable speed three roller peristaltic pump (not shown), together with a pump speed adjuster and a flowmeter (0.1 to 1.5 litres/hour), for determining, controlling and indicating the flow rate of corrosive ionised solution to the atomising nozzle 19.

A roof unit 45 is mounted on the frame 1 in a manner which facilitates controlled opening and closing of the roof unit. The roof unit 45 is shown in a closed position in FIG. 1 and in an open position in FIG. 2, the roof unit being supported by arms 47 and 49 which are pivotably mounted on the roof unit 45 and on the frame 1. In the closed position of the roof unit 45, the roof unit closes the chamber 11, while in the open position the roof unit is positioned generally horizontally above the chamber to permit ready access to the interior of the chamber.

A control panel (not shown) is provided on the fascia of a small console mounted on the cabinet framework on either the left-hand or the right-hand side. The control panel incorporates a number of switches and indicators (such as indicator lights) that inform the operator which environmental cycle the cabinet is currently performing.

A safety switch (not shown) is incorporated into the cabinet disabling all primary control circuits until the roof unit is in a fully closed position.

A microprocessor-based controller/programmer stores up to twenty programs, which can comprise any of the available environmental cycles in any sequence. Any one of the programs can be selected, loaded and run as and when required.

Movement of the roof unit 45 is by way of a pneumatic cylinder (not shown) pivotably mounted to both the roof unit 45 and the frame 1 at each end of the cabinet. Operation of the cylinders is controlled by way of an up/down select switch (not shown). When a signal to raise the roof unit is given by way of the up/down switch, a valve (not shown) is energised to supply a flow of compressed air regulated at a pressure in the range from 4 to 6 bar to the pneumatic cylinders, allowing the piston rod of each cylinder to extend upwardly to its full extent.

As the piston rods raise the roof unit 45, at approximately half way to full extension the arms 47, 49 cause the roof unit to pivot and to swivel to a generally horizontal configuration above the chamber 11. The compressed air supply to the pneumatic cylinders includes a non-return valve (not shown) which is activated in the event of loss of power in order to prevent the roof unit closing. The compressed air supply also includes air flow control valves (not shown) in order to effect smooth raising and lowering of the roof unit, together with cushioning in the final stages of raising and lowering.

Figure 2:
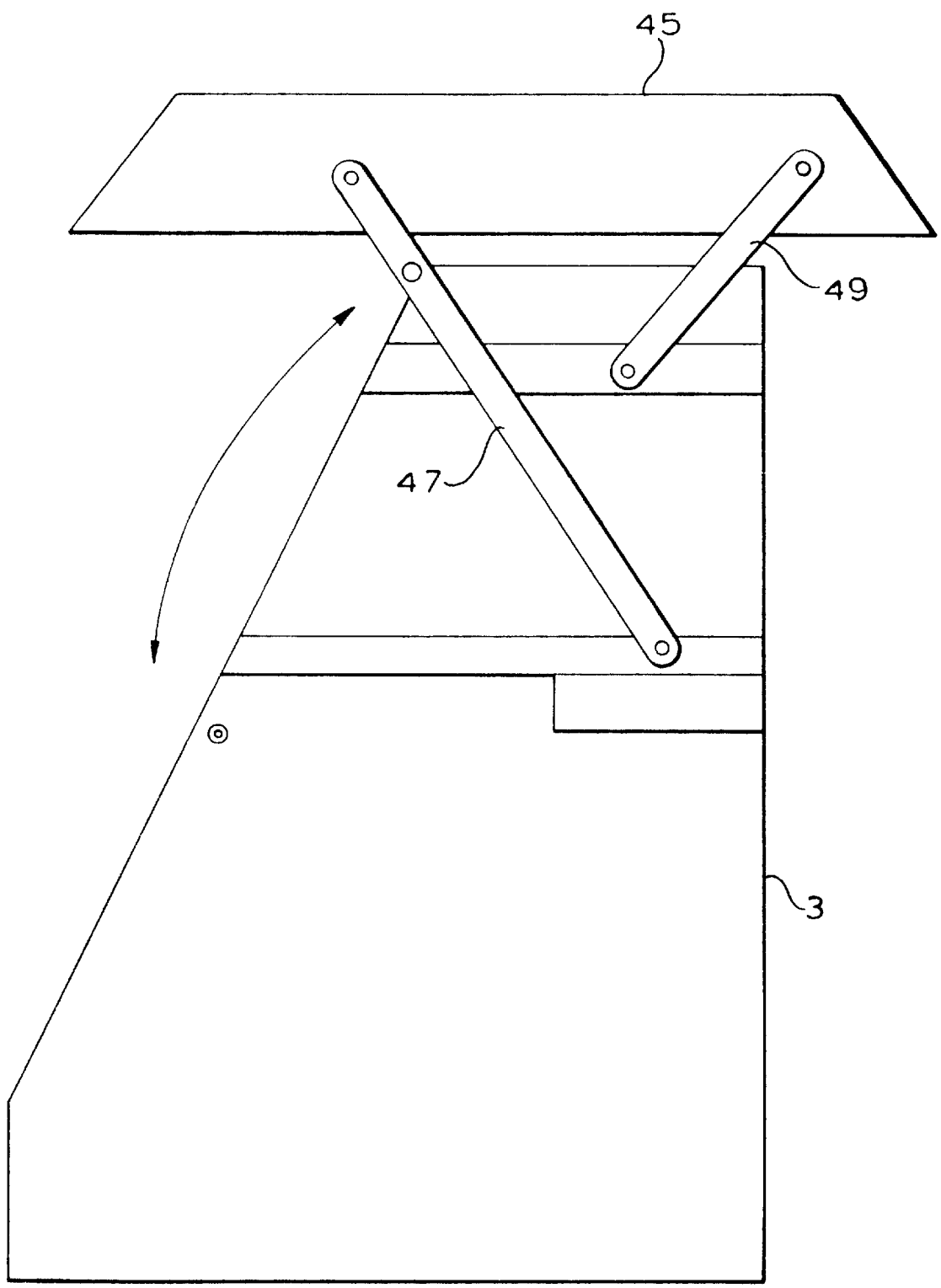
FIG. 2 is a side elevational view of an upper part of the environmental cabinet shown in FIG. 1, with a cover of the cabinet in an open position.
Figure 5:
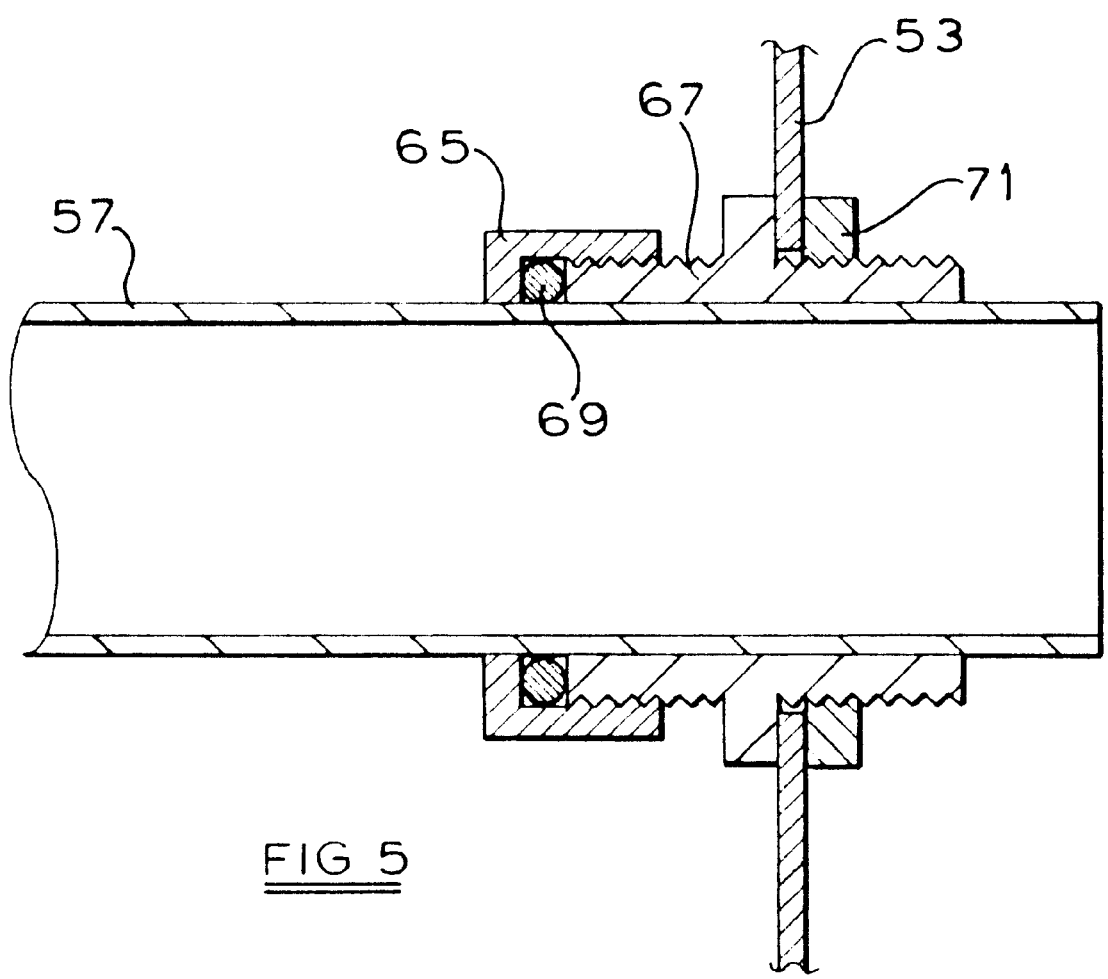
FIG. 5 is a diagrammatic cross-sectional view through a seal between a tubular sleeve and the inner end plate of the cover.

The roof unit is shown in FIGS. 1 and 2 and in more detail in FIGS. 3, 4 and 5. The roof unit 45 is generally in the form of a trough, for example of mild steel sheet, containing an inner casing 50, for example of polypropylene material. The trough is provided with detachable or hinged outer end plates 51, while the inner casing is provided with fixed inner end plates 53. The outer end plates 51 permit access to the ends of a number of lamps 55 mounted within the roof unit 45.

Extending between the inner end plates 53 within the trough of the roof unit 45 is a plurality, eight as illustrated, of generally horizontal tubes 57 of material transparent at least in a wavelength range in which it is desired to irradiate the sample material. For example, for ultra-violet and/or infra-red wavelengths the tubes may be made of fused quartz, such as Type 214 clear fused quartz.

The tubes 57 are sealed to the inner end plates 53 of the inner casing 50 by means of hermetic seals 59, for example of nylon material. This ensures no egress of moisture or corrosive material to the terminations (not shown) of the lamps 55 intermediate the inner end plates 53 and the outer end plates 51. The seals are shown diagrammatically in FIG. 6 and comprise two threaded members 65 and 67 for compressing therebetween an elastomeric, for example rubber, seal 69 such that the seal is urged against the external surface of the tube 57. The seals are secured to the inner end plates with the aid of a lock nut 71.

The lamps 55 are in the form of elongate fluorescent tubes which may emit, for example, ultra-violet light of UVA radiation in the wavelength range from 315 to 400 nm and/or UVB radiation in the wavelength range from 280 to 315 nm. Alternatively or additionally, the lamps could emit electromagnetic radiation in the visible and/or infra-red regions of the spectrum.

The lamps 55 are supported axially within the tubes 57 by a tubular collar 60 provided in the region of each end of each lamp. The tubular collar 60 may be made of a suitable plastics material and is provided with a plurality of radial flanges which extend between the lamps 55 and the internal wall of the tube 57 so as to support the lamp in a manner which permits the passage of air between the lamp and the tube.

The lamps 55 are cooled with the aid of fans 62 mounted in the roof unit 45 intermediate the inner end plates 53 and the outer end plates 51. The fans draw ambient air into the space between one of the inner end plates 53 and one of the outer end plates 51, pass the air through the tubes 57 such that it flows over the surfaces of the lamps 55 to cool the same, and draw air from the tubes 57 and exhaust the same into the space between the other of the inner end plates 53 and the other of the outer end plates 51. The fans may be, for example, 24 volt DC axial fans which pass air through the tubes 57 at a rate of about 50 litres/second.

If desired, reflectors (not shown) may be positioned between the tubes 55 and the inner casing 50 of the roof unit 45 to reflect radiation towards the sample material.

Strips 61, for example generally planar strips of plastics material such as polypropylene, extend within the inner casing 50 in the axial direction of the tubes 57. The strips are mounted at an angle of about 30 degrees to the horizontal and extend to beneath each of the tubes 57, terminating a distance of about 30 mm beneath each tube. Each strip 61 is provided with a row of holes (not shown) extending in use along the axial centre line of the tube 57 positioned beneath the respective strip 61.

The strips 61 form a cascade system which allows a cleaning fluid such as water, released from an elongate sprinkler 63 positioned above to uppermost strip 61, to flow downwardly on to the tube 57 below. The water runs at a relatively slow rate around the front and rear of each tube 57 and then drops on to the next strip below, repeating the process until all the tubes 57 have been rinsed with clean water.

Each strip 61 extends outwardly from the inner casing 50 a sufficient distance to prevent water from the cascade system falling onto the sample material, but not so far as to prevent each lamp 55 emitting a substantial amount of radiation onto the sample material.

The described environmental chamber provides five cycles, a fog (or mist) cycle, a rinse cycle, a radiation cycle, a humidity cycle and a dry cycle.

The fog cycle employs a corrosive ionised aqueous solution selected from one or more of salt (sodium chloride), ammonium sulphate, acid (such as acetic acid) and alkali (such as sodium hydroxide). During the fog cycle, the drain valve 31 is in its open position and assists in venting the exhausted compressed air and allows excess corrosive solution to drain away. The side wall heaters are energised to provide a desired temperature in the chamber 11 in the range from ambient to 60° C.

Corrosive solution is drawn from a reservoir by the peristaltic pump and is pumped to the atomising nozzle 19 at a flow rate in the range from 0.35 to 0.6 litres/hour. Compressed air is supplied to the atomising nozzle 19 at a regulated pressure in the range from 15 to 18 psi (1.1 to 1.3 bar) and the nozzle generates a fine mist (fog). When the fog cycle commences, the upper portion of the chamber 11 fills with corrosive fog. If desired, the atomising nozzle 19 can be swivelled in a forwards or backwards direction to direct the fog in a predetermined direction.

Within minutes, the corrosive fog travels into the area above the sample rack where the test samples are positioned and some of the fog settles on the test samples.

The rate of generation of the fog is monitored with the aid of a number of collection vessels, each of a diameter of 100 mm and totalling 80 $cm^2$, to establish the desired collection rate in the range from 0.5 to 4.0 ml/hour. The collection rate can be adjusted by increasing or decreasing the flowrate of the corrosive solution by increasing or decreasing the pump speed. Additionally or alternatively, the air pressure can be adjusted.

In order to avoid cross-contamination of the test samples, the used corrosive solution not collected in the collection vessels is allowed to drain into the lower portion of the chamber and to flow away down the drain 29 to a foul water drainage system (not shown).

When the fog cycle has completed, an air purge is conducted for a few minutes in order to evacuate the fog present in the chamber at the end of the cycle.

The fog cycle is always followed by the rinse cycle in order to remove deposits of the corrosive solution from the tubes 57. The rinse cycle is initiated by opening a solenoid valve (not shown) which allows a cleaning fluid to enter the cascade system at the top of the roof unit 45.

As described above, the strips 61 with the holes formed therein allow cleaning fluid to flow downwardly on to the tube 57 below. The cleaning fluid runs at a relatively slow rate around the front and rear of each tube 57 and then drops on to the next strip below, repeating the process until all the tubes 57 have been rinsed with cleaning fluid.

The strips 61 extend outwardly from the inner casing 50 a sufficient distance to prevent cleaning fluid from the cascade system falling onto the sample material.

The cleaning fluid, after flowing around the lowermost tube 57, falls into the lower portion of the chamber 11 and down the drain 29 to the foul water drainage system.

For the radiation cycle, the cooling fans 62 are energised and pass cooling air between the lamps 55 and the tubes 57. The lamps 55 are also energised and emit radiation on to the test samples which are generally positioned about 120 mm from the lamps.

The side wall heaters are energised to provide a desired temperature in the chamber 11 in the range from ambient to 60° C. However, less energy may be required during the radiation cycle than during the fog cycle due to the heat generated by the lamps.

Upon completion of the radiation cycle the lamps and the cooling fans are de-energised.

For the humidity cycle, the drain valve 31 is closed and the lower portion of the chamber (the humidity bath) is filled with water by way of the inlet 23 until the float switch 25 indicates a maximum desired water level has been reached.

The heater 27 is then energised to heat the water and produce water vapour which is directed upwardly towards the test samples by means of compressed air issuing from a series of air purge nozzles 21 supplied by a manifold (not shown) positioned externally of the lower portion of the chamber 11. The compressed air is regulated to a pressure in the range of about 6 to 8 psi (0.4 to 0.6 bar). Air is removed from the upper region of the chamber by means of two upper vents (or drains) 35.

As an alternative to the heater 27, an ultrasonic transducer (not shown) may be employed to generate water vapour.

The water vapour can be condensing or non-condensing as desired. The humidity levels can be in the range from 20% to 97% relative humidity to saturation and can be controlled as required.

During the course of the humidity cycle, should the water level in the humidity bath drop below a minimum desired water level due to evaporation, the float switch 25 opens and the humidity bath is refilled to the maximum desired water level.

However, should the level of water in the humidity bath fall below the minimum desired water level a safety switch (not shown) operates to de-energise the heater 27.

When the humidity cycle has completed its programmed time duration, air supply to the manifold is terminated and the drain valve 31 is opened to allow the humidity bath to empty.

The environmental cabinet according to the present invention not only enables a sample material to be exposed to a corrosive solution and to electromagnetic radiation in a manner which does not lead to corrosion of the electrical power supply to the source of electromagnetic radiation, but additionally permits the source of electromagnetic radiation to be replaced when it reaches the end of its service life.

We claim:

1. An environmental cabinet for simulating the effects of extended outdoor weathering on a sample material, the outdoor weathering effects including subjecting the sample material to cycles of at least the application of a corrosive solution and exposure to electromagnetic radiation, wherein the cabinet comprises:

a chamber for containing a sample material to be tested;

a source of electromagnetic radiation for subjecting the sample material within the chamber to cycles of radiation;

spray means for providing a cyclic spray of a corrosive solution to be deposited on the sample material within the chamber; and control means for subjecting the sample material within the chamber to electro-magnetic radiation and corrosive solution in a cyclic manner, wherein the source of electromagnetic radiation is disposed within a radiation transparent shield passing through the chamber and sealed thereto, and means is provided for passing air between the source of electromagnetic radiation and the shield.

2. An environmental cabinet according to claim 1, wherein the source of electromagnetic radiation is mounted in an openable cover of the chamber.

3. An environmental cabinet according to claim 1, wherein the source of electromagnetic radiation is generally cylindrical.

4. An environmental chamber according to claim 3, wherein the source of electromagnetic radiation is in the form of a tubular lamp.

5. An environmental cabinet according to claim 1, wherein the source of electromagnetic radiation is adapted to emit radiation selected from the group consisting of ultraviolet and infra-red.

6. An environmental cabinet according to claim 5, wherein the ultra violet radiation is in the range from about 280 to about 400 nm.

7. An environmental cabinet according to claim 6, wherein the ultra violet radiation is in the range from about 280 to about 315 nm.

8. An environmental cabinet according to claim 6, wherein the ultra violet radiation is in the range from about 315 to about 400 nm.

9. An environmental cabinet according to claim 1, wherein the radiation transparent shield is in the form of a sleeve with the source of electromagnetic radiation extending therethrough.

10. An environmental cabinet according to claim 9, wherein the radiation transparent shield is in the form of a tubular sleeve.

11. An environmental cabinet according to claim 9, wherein spacer means is provided to support the source of electromagnetic radiation in a spaced manner within the sleeve.

12. An environmental cabinet according to claim 1, wherein means is provided for passing a cleaning fluid over the outer surface of the radiation transparent shield.

13. An environmental cabinet according to claim 12, wherein the means for passing cleaning fluid over the outer surface of the radiation transparent shield comprises a sprinkler.

14. An environmental cabinet according to claim 12 and including a plurality of sources of radiation and a plurality of radiation transparent shields, wherein means is provided for accumulating the cleaning fluid passing over one radiation transparent shield and for distributing the cleaning fluid over a further radiation transparent shield.

15. An environmental cabinet according to claim 14, wherein the radiation transparent shields are arranged generally one above the other, the accumulating and distributing means comprising an inclined member positioned beneath one radiation transparent shield and adapted to receive cleaning fluid from the one radiation transparent shield, the inclined member being provided with a plurality of apertures for distributing accumulated cleaning fluid over a further radiation transparent shield disposed therebeneath.

16. An environmental cabinet for simulating the effects of extended outdoor weathering on a sample material, the outdoor weathering effects including subjecting the sample material to cycles of at least the application of a corrosive solution and exposure to electromagnetic radiation, wherein the cabinet comprises:

a chamber for containing a sample material to be tested;

a source of electromagnetic radiation for subjecting the sample material within the chamber to cycles of radiation;

spray means for providing a cyclic spray of a corrosive solution to be deposited on the sample material within the chamber; and control means for subjecting the sample material within the chamber to electromagnetic radiation and corrosive solution in a cyclic manner, wherein the source of electromagnetic radiation is disposed within a radiation transparent shield passing through the chamber and sealed thereto, the radiation transparent shield being in the form of a sleeve with the source of electromagnetic radiation extending therethrough.

17. An environmental cabinet according to claim 16, wherein the radiation transparent shield is in the form of a tubular sleeve.

18. An environmental cabinet according to claim 16, wherein spacer means is provided to support the source of electromagnetic radiation in a spaced manner within the sleeve.

19. An environmental cabinet according to claim 16, wherein the source of electromagnetic radiation is mounted in an openable cover of the chamber.

20. An environmental chamber according to claim 16, wherein the source of electromagnetic radiation is in the form of a tubular lamp.

21. An environmental cabinet according to claim 16, wherein the source of electromagnetic radiation is adapted to emit radiation selected from the group consisting of ultraviolet and infra-red.

22. An environmental cabinet according to claim 21, wherein the ultra-violet radiation is in the range from about 280 to about 400 nm.

23. An environmental cabinet for simulating the effects of extended outdoor weathering on a sample material, the outdoor weathering effects including subjecting the sample material to cycles of at least the application of a corrosive solution and exposure to electromagnetic radiation, wherein the cabinet comprises:

a chamber for containing a sample material to be tested;

a source of electromagnetic radiation for subjecting the sample material within the chamber to cycles of radiation;

spray means for providing a cyclic spray of a corrosive solution to be deposited on the sample material within the chamber; and control means for subjecting the sample material within the chamber to electromagnetic radiation and corrosive solution in a cyclic manner, wherein the source of electromagnetic radiation is disposed within a radiation transparent shield passing through the chamber and sealed thereto, and means is provided for passing a cleaning fluid over the outer surface of the radiation transparent shield.

24. An environmental cabinet according to claim 23, wherein the means for passing cleaning fluid over the outer surface of the radiation transparent shield comprises a sprinkler.

25. An environmental cabinet according to claim 23 and including a plurality of sources of radiation and a plurality of radiation transparent shields, wherein means is provided for accumulating the cleaning fluid passing over one radiation transparent shield and for distribution of the cleaning fluid over a further radiation transparent shield.

26. An environmental cabinet according to claim 25, wherein the radiation transparent shields are arranged generally one above the other, the accumulating and distribution means comprising an inclined member positioned beneath one radiation transparent shield and adapted to receive cleaning fluid from the one radiation transparent shield, the inclined member being provided with a plurality of apertures for distributing accumulated cleaning fluid from the one radiation transparent shield, the inclined member being provided with a plurality of apertures for distributing accumulated cleaning fluid over a further radiation transparent shield disposed therebeneath.

27. An environmental cabinet according to claim 23, wherein the source of electromagnetic radiation is mounted in an openable cover of the chamber.

28. An environmental chamber according to claim 23, wherein the source of electromagnetic radiation is in the form of a tubular lamp.

29. An environmental cabinet according to claim 23, wherein the source of electromagnetic radiation is adapted to emit radiation selected from the group consisting of ultra-violet and infra-red.

30. An environmental cabinet according to claim 29, wherein the ultra-violet radiation is in the range from about 280 to about 400 nm.

* * * * *